(12) United States Patent
Lewandowski et al.

(10) Patent No.: US 9,828,489 B2
(45) Date of Patent: Nov. 28, 2017

(54) PLASTICIZED POLYMERIC COMPOSITION

(71) Applicant: 3M INNOVATIVE PROPERTIES COMPANY, St. Paul, MN (US)

(72) Inventors: Kevin M. Lewandowski, Inver Grove Heights, MN (US); Jonathan E. Janoski, Woodbury, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 14/914,185

(22) PCT Filed: Sep. 8, 2014

(86) PCT No.: PCT/US2014/054513
§ 371 (c)(1),
(2) Date: Feb. 24, 2016

(87) PCT Pub. No.: WO2015/038463
PCT Pub. Date: Mar. 19, 2015

(65) Prior Publication Data
US 2016/0200896 A1    Jul. 14, 2016

Related U.S. Application Data

(60) Provisional application No. 61/876,951, filed on Sep. 12, 2013.

(51) Int. Cl.
| | | |
|---|---|---|
| *C08J 3/09* | (2006.01) | |
| *C08K 5/15* | (2006.01) | |
| *D21H 17/17* | (2006.01) | |
| *C08K 5/1535* | (2006.01) | |
| *C07D 307/02* | (2006.01) | |
| *C08J 5/18* | (2006.01) | |
| *C07D 307/24* | (2006.01) | |
| *C07D 307/68* | (2006.01) | |

(52) U.S. Cl.
CPC .......... *C08K 5/1535* (2013.01); *C07D 307/24* (2013.01); *C07D 307/68* (2013.01); *C08J 5/18* (2013.01); *C08J 2301/12* (2013.01); *C08J 2367/04* (2013.01)

(58) Field of Classification Search
None
See application file for complete search history.

(56) References Cited

U.S. PATENT DOCUMENTS

| | | |
|---|---|---|
| 3,259,636 A | 7/1966 | Lew |
| 4,620,026 A | 10/1986 | Siegel |
| 7,166,654 B2 | 1/2007 | Fujita |
| 7,498,372 B2 | 3/2009 | Schaefer |
| 2004/0030175 A1* | 2/2004 | Disteldorf ............... C07C 67/08 560/98 |
| 2009/0176917 A1 | 7/2009 | Lubker |
| 2013/0331491 A1 | 12/2013 | Becker |
| 2015/0033985 A1 | 2/2015 | Kavanagh |

FOREIGN PATENT DOCUMENTS

| | | |
|---|---|---|
| CN | 102093212 | 6/2011 |
| WO | WO 2012/113608 | 8/2012 |

OTHER PUBLICATIONS

Hoydonckx, "Furfural and Derivatives", Ullmann's Encyclopedia of Industrial Chemistry, 2012, vol. 16, pp. 285-313.
Sanderson, "Synthesis and Evaluation of Dialkyl Furan-2,5-Dicarboxylates as Plasticizers for PVC", Journal of Applied Polymer Science, Sep. 1994, vol. 53, No. 13, pp. 1785-1793, XP000464476.
International Search Report for PCT International No. PCT/US2014/054513, dated Nov. 10, 2014, 4 pages.

* cited by examiner

*Primary Examiner* — Robert T Butcher
(74) *Attorney, Agent, or Firm* — Jean A. Lown

(57) ABSTRACT

Polymeric compositions are provided that include a furan 2,5-di-ester or tetrahydrofuran 2,5-di-ester plasticizer. The plasticizer has low odor, has good compatibility with a variety of polymers such as hydrophilic polymeric materials, and can be formed from renewable resources. Further, the plasticizer can be used at temperatures often encountered during hot melt processing of polymeric compositions.

10 Claims, No Drawings

PLASTICIZED POLYMERIC COMPOSITION

CROSS REFERENCE TO RELATED APPLICATIONS

This application is a national stage filing under 35 U.S.C. 371 of PCT/US2014/054513, filed Sep. 8, 2014, which claims the benefit of U.S. Provisional Application No. 61/876951, filed Sep. 12, 2013, the disclosure of which is incorporated by reference in its/their entirety herein.

TECHNICAL FIELD

Polymeric compositions that include a furan 2,5-di-ester or a tetrahydrofuran 2,5-di-ester plasticizer and articles that include the polymeric compositions are provided.

BACKGROUND

Various ester compounds have been used as plasticizers in polymeric compositions. These plasticizers include, for example, alkyl phthalates and adipate esters. In recent years, various plasticizers based on renewable materials have been introduced. These include those based on citric acid (e.g., from Vertellus), succinic acid (e.g., from BioAmber and Myriant), vegetable oil (e.g., from Danisco and Dow Chemical Co.), isosorbide (e.g., from Roquette), and levulinic acid (e.g., from Segetis). Most of these renewable materials are compatible with polyvinyl chloride but may not be suitable for use with more hydrophilic polymers.

SUMMARY

Polymeric compositions are provided that include a furan 2,5-di-ester or tetrahydrofuran 2,5-di-ester plasticizer. The plasticizer has low odor, has good compatibility with a variety of polymeric materials, and can be formed from renewable resources. Further, the plasticizer can be used at temperatures often encountered during hot melt processing of polymeric compositions.

In a first aspect, a polymeric composition is provided that includes a) a plasticizer and b) a polymeric material, wherein the plasticizer is compatible with the polymeric material. The plasticizer is a compound of Formula (I).

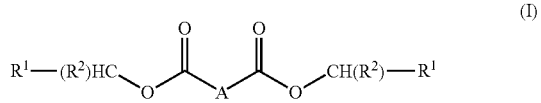

In Formula (I), group A is a divalent group

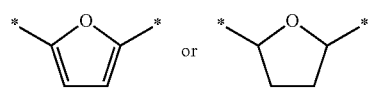 [SMILES: *c1ccc(*)o1 ; *C1CCC(*)O1]

where an asterisk (*) indicates where the divalent group A is connected to the rest of the compound. The group $R^1$ is a heteroalkyl having at least one oxy group. The group $R^2$ is hydrogen or an alkyl.

In a second aspect, an article is provided that includes a polymeric composition. The polymeric composition is the same as described above.

DETAILED DESCRIPTION

Polymeric compositions are provided that include a polymeric material plus a furan 2,5-di-ester, a tetrahydrofuran 2,5-di-ester, or a combination thereof. The furan 2,5-di-ester and/or tetrahydrofuran 2,5-di-ester can function as a plasticizer for various compatible polymeric materials such as hydrophilic polymeric materials.

The terms "a", "an", "the", "at least one", and "one or more" are used interchangeably.

The term "and/or" means one or both such as the expression A and/or B refers to A alone, B alone, or both A and B.

The terms "polymeric material" and "polymer" are used interchangeably and can refer to a homopolymer, copolymer, terpolymer, and the like.

The term "heteroalkyl" refers to an alkyl having one or more catenary oxygen. The heteroalkyl can be linear, branched, cyclic, or a combination thereof. The catenary oxygen can be in a linear, branched, or cyclic portion of the heteroalkyl. The heteroalkyl is often an alkoxy group, ether group, or polyether group.

The term "alky" refers to a monovalent radical of an alkane. Suitable alkyl groups can have up to 10 carbon atoms, up to 6 carbon atoms, up to 4 carbon atoms, or up to 3 carbon atoms. The alkyl group can be linear, cyclic, or branched.

The term "alkylene" refers to a divalent radical of an alkane. Suitable alkylene groups can have up to 10 carbon atoms, up to 6 carbon atoms, up to 4 carbon atoms, or up to 3 carbon atoms.

In a first aspect, a polymeric composition is provided that includes a) a plasticizer and b) a polymeric material, wherein the plasticizer is compatible with the polymeric material. The plasticizer is a compound of Formula (I).

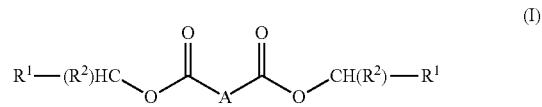

In Formula (I), group A is a divalent group

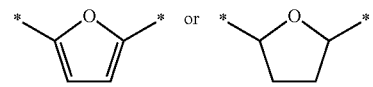 [SMILES: *c1ccc(*)o1 ; *C1CCC(*)O1]

where an asterisk indicates where the divalent group A is connected to the rest of the compound. The group $R^1$ is a heteroalkyl having at least one oxy group. The group $R^2$ is hydrogen or an alkyl.

The plasticizer (i.e., compound) of Formula (I) is a furan 2,5-diester of Formula (IA) or a tetrahydrofuran 2,5-di-ester of Formula (IB).

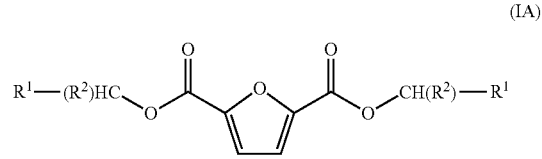

-continued

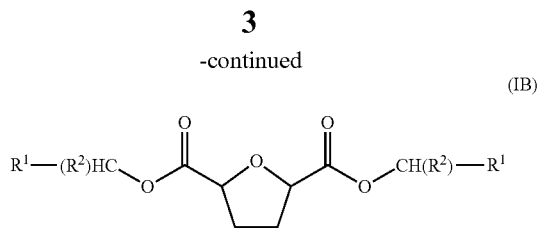

(IB)

The compounds of Formula (IA) and (IB) include all possible stereoisomers.

Each $R^1$ group in Formulas (I), (IA), and (IB) is a heteroalkyl and typically has up to 20 carbon atoms, up to 16 carbon atoms, up to 10 carbon atoms, up to 8 carbon atoms, up to 6 carbon atoms, up to 4 carbon atoms, or up to 3 carbon atoms and up to 6 oxygen atoms, up to 4 oxygen atoms, or up to 2 oxygen atoms. The group $R^1$ can be linear, branched, cyclic, or a combination thereof. The two $R^1$ groups can be the same or different but are often identical.

In some embodiments, the heteroalkyl $R^1$ group can be of formula $-(R^a)_p-(O-R^b)_q-O-R^c$ where $R^a$ and $R^b$ are each an alkylene, $R^c$ is an alkyl, p is an integer equal to 0 or 1, and q is an integer in a range of 0 to 4. Each $R^a$, each $R^b$, and each $R^c$ group independently can have up to 4 carbon atoms, up to 3 carbon atoms, or up to 2 carbon atoms. The number of oxy groups is often in the range of 1 to 5, in the range of 1 to 4, or in the range of 1 to 3. Some example heteroalkyl groups include, but are not limited to, $-CH_2-O-CH_3$, $-CH_2-O-CH_2CH_3$, $-CH_2-O-CH_2CH_2CH_3$, $-CH_2-O-CH(CH_3)_2$, $-CH_2-O-CH_2CH_2CH_2CH_3$, $-CH_2-O-CH_2CH_2-O-CH_3$, $-CH_2-O-CH_2CH_2-O-CH_2CH_3$, $-CH_2-O-CH_2CH_2-O-CH_2CH_2CH_3$, $-CH_2-O-CH_2CH_2-O-CH(CH_3)_2$, $-CH_2-O-CH_2CH_2-O-CH_2CH_2CH_2CH_3$, $-CH_2CH_2-O-CH_3$, $-CH_2CH_2-O-CH_2CH_3$, $-CH_2CH_2-O-CH(CH_3)_2$, $-CH_2CH_2-O-CH_2CH_2CH_3$, $-CH_2CH_2-O-CH_2CH_2CH_2CH_3$, $-CH_2CH_2-O-CH_2CH_2CH_2-O-CH_3$, $-CH_2CH_2-O-CH_2CH_2CH_2-O-CH_2CH_3$, $-CH_2CH_2-O-CH_2CH_2CH_3$, $-CH_2CH_2-O-CH_2CH_2CH_3$, $-CH_2CH_2CH_2-O-CH(CH_3)_2$, and $-CH_2-O-CH_2CH_2CH_2-O-CH_2CH_2CH_2CH_3$.

In other embodiments, the heteroalkyl can include a cyclic group with the catenary oxygen being part of the cyclic group. For example, the heteroalkyl can include a tetrahydrofuranyl or tetrahydropyranyl group.

Each $R^2$ group in Formulas (I), (IA), and (IB) is hydrogen or an alkyl. The alkyl group typically has up to 10 carbon atoms, up to 6 carbon atoms, or up to 3 carbon atoms. For example the alkyl often has 1 to 10 carbon atoms, 3 to 10 carbon atoms, 1 to 6 carbon atoms, or 1 to 4 carbon atoms.

In some embodiments, the compound of Formula (I) is selected from one or more of the following compounds.

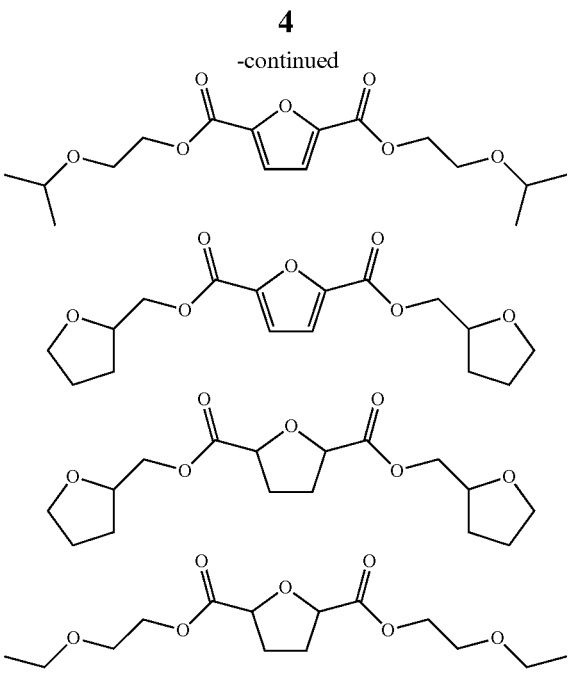

Compounds of Formula (IA) can be prepared using any suitable synthesis approach. For example, these compounds can be prepared using a one-step transesterification reaction of 2,5-dimethyl furan dicarboxylate, which is commercially available, with an alcohol of formula $R^1-CH(R^2)-OH$ in the presence of a catalyst as shown in Reaction Scheme A.

Reaction Scheme A

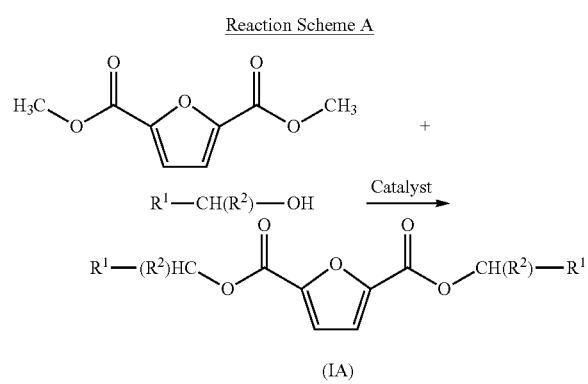

(IA)

Suitable catalysts for the tranesterification reaction include, for example, metal alkoxides (e.g., antimony alkoxides and magnesium alkoxides), tetraalkyl titanates (e.g., tetrabutyl titanate), protonic acids (e.g., sulfuric acid, perchloric acid, and para-toluene sulfonic acid), metal oxides (e.g., antimony oxides and zeolites), and tin salts. Compounds of Formula (IB) can be prepared in a similar manner to those of Formula (IA) but with the addition of a hydrogenation step prior to the transesterification reaction. That is, the 2,5-dimethyl furan dicarboxylate is hydrogenated to 2,5-dimethyl tetrahydrofuran dicarboxylate prior to transesterification. The product of the transesterification reaction (i.e., a compound of Formula (IA) or (IB)) is typically isolated by distillation. The yields are typically greater than about 70 percent. Further details of the various reactions are included in the Example section.

Any alcohol of formula $R^1-CH(R^2)-OH$ can be used in Reaction Scheme A. Some example alcohols include, but are not limited to, ethylene glycol monomethyl ether HO—$CH_2CH_2$—O—$CH_3$, ethylene glycol monoethyl ether HO—$CH_2CH_2$—O—$CH_2CH_3$, ethylene glycol monopropyl ether HO—$CH_2CH_2$—O—$CH_2CH_2CH_3$, ethylene glycol monoisopropyl ether HO—$CH_2CH_2$—O—$CH(CH_3)_2$, ethylene glycol monobutyl ether HO—$CH_2CH_2$—O—$CH_2CH_2CH_2CH_3$, diethylene glycol monomethyl ether HO—$CH_2CH_2$—O—$CH_2CH_2$—O—$CH_3$, diethylene glycol monoethyl ether HO—$CH_2CH_2$—O—$CH_2CH_2$—O—$CH_2CH_3$, diethylene glycol monopropyl ether HO—$CH_2CH_2$—O—$CH_2CH_2$—O—$CH_2CH_2CH_3$, diethylene glycol monoisopropyl ether HO—$CH_2CH_2$—O—$CH_2CH_2$—O—$CH(CH_3)_2$, diethylene glycol monobutyl ether HO—$CH_2CH_2$—O—$CH_2CH_2$—O—$CH_2CH_2CH_2CH_3$, propylene glycol monomethyl ether HO—$CH_2CH_2CH_2$—O—$CH_3$, propylene glycol monoethyl ether HO—$CH_2CH_2CH_2$—O—$CH_2CH_3$, propylene glycol monoisopropyl ether HO—$CH_2CH_2CH_2$—O—$CH(CH_3)_2$, propylene glycol monopropyl ether HO—$CH_2CH_2CH_2$—O—$CH_2CH_2CH_3$, propylene glycol monobutyl ether HO—$CH_2CH_2CH_2$—O—$CH_2CH_2CH_2CH_3$, dipropylene glycol monomethyl ether HO—$CH_2CH_2CH_2$—O—$CH_2CH_2CH_2$—O—$CH_3$, dipropylene glycol monoethyl ether HO—$CH_2CH_2CH_2$—O—$CH_2CH_2CH_2$—O—$CH_2CH_3$, dipropylene glycol monopropyl ether HO—$CH_2CH_2CH_2$—O—$CH_2CH_2CH_2$—O—$CH_2CH_2CH_3$, dipropylene glycol monoisopropyl ether HO—$CH_2CH_2CH_2$—O—$CH_2CH_2CH_2$—O—$CH(CH_3)_2$, dipropylene glycol monobutyl ether HO—$CH_2CH_2CH_2$—O—$CH_2CH_2CH_2$—O—$CH_2CH_2CH_2CH_3$, tetrahydrofuryl alcohol and furyl alcohol.

The compounds of Formula (I) can be prepared from a plant-based material (i.e., a renewable material). More particularly, these compounds can be derived from the renewable material 2,5-furan dicarboxylic acid (FDCA). FDCA can be produced by dehydration of C-6 sugars such as fructose to the intermediate hydroxyl methyl furfural. This intermediate can be oxidized to FDCA. The FDCA can be converted to an acid chloride and then reacted with the alcohol $R^1$—$CH(R^2)$—OH. Alternatively, the FDCA can be methylated (by reaction with methanol) and then transesterified with an alcohol having a higher molecular weight.

In some embodiments, the alcohol $R^1$—$CH(R^2)$—OH can be a renewable material as well. For example, the alcohol can be tetrahydrofurfuryl alcohol. This alcohol can be formed from C5 sugars (i.e., sugars having 5 carbon atoms). The C5 sugars can be dehydrated to furfural (i.e., 2-furaldehyde or furfuraldehyde) and then hydrogenated to furfuryl alcohol. Furfuryl alcohol can be further hydrogenated with a nickel catalyst to tetrahydrofurfuryl alcohol. Methods of preparing tetrahydrofurfuryl alcohol are further described in the reference Hoydonckx et al., Furfural and Derivatives, *Ullmann's Encyclopedia of Industrial Chemistry*, Wiley-VCH Verlag GmbH & Co., pp. 285-313 (2012).

The compound of Formula (I) is combined with a compatible polymeric material to provide a polymeric composition. As used herein, the term "compatible" refers to a polymeric material that is miscible with the compounds of Formula (I). Compatibility can be determined, for example, by measuring the haze of a film prepared from a mixture of the polymeric material and the compound of Formula (I). One suitable method of measuring Haze is described in Example section (Measurement of Haze). A low haze value (e.g., less than 5, less than 4, less than 3, less than 2, or even less than 1) is typically associated with a mixture having compatible components.

Many polymeric materials are compatible with the compounds of Formula (I). The polymeric material can be hydrophilic. Example polymeric materials include various thermoplastic polymers such as various aliphatic polyesters (e.g., polylactic acid), cellulose esters, polyvinyl chloride, and various acrylic polymers such as poly(methyl methacrylate). Other example polymeric materials include various elastomeric polymers such as those included in adhesive compositions. The elastomeric polymers are often acrylic polymers such as polymers formed using at least one alkyl (meth)acrylate and optionally a polar monomer such as (meth)acrylic acid.

The aliphatic polyesters can be formed by dehydration-polycondensation reactions of one or more aliphatic hydroxycarboxylic acids. Example hydroxycarboxylic acids include, but are not limited to, L-lactic acid, D-lactic acid, glycolic acid, 3-hydroxypropionic acid, 3-hydroxybutyric acid, 4-hydroxybutyric acid, 4-hydroxypentanoic acid, 3-hydroxypentanoic, 5-hydroxypentanoic acid, 3-hydroxyhexanoic acid, 6-hydroxyhexanoic acid, 3-hydroxyheptanoic, 3-hydroxyoctanoic acid, or mixtures thereof.

Alternatively, the aliphatic polyesters can be formed by dehydration-polycondensation reactions of a mixture containing an aliphatic polycarboxylic acid (i.e., a compound having two or more carboxylic acid groups) and an aliphatic polyol (i.e., a compound having two or more hydroxyl groups). Examples of polycarboxylic acids include, but are not limited to, oxalic acid, succinic acid, malonic acid, glutaric acid, adipic acid, pimelic acid, suberic acid, azelaic acid, undecanedioic acid, dodecanedioic acid, and anhydrides thereof. Examples of polyols include, but are not limited to, ethylene glycol, diethylene glycol, triethylene glycol, polyethylene glycol, polypropylene glycol, 1,3-propanediol, 1,2-propanediol, dipropylene glycol, 1,2-butanediol, 1,3-butanediol, 1,4-butanediol, 3-methyl-1,5-pentanediol, 1,6-hexanediol, 1,9-nonanediol, neopentyl glycol, tetramethylene glycol and 1,4-cyclohexanedimethanol. Suitable polycarboxylic acids often have two carboxylic acid group and suitable polyols often have two hydroxyl groups.

The aliphatic polyester can be a polylactic acid based resin (PLA-based resin). Some example PLA-based resins can be formed from L-lactic acid, D-lactic acid, or a mixture thereof. Other example PLA-based resins can be prepared from L-lactic acid, D-lactic acid, or a mixture thereof in combination with at least one aliphatic hydroxycarboxylic acid (other than lactic acid). Yet other PLA-based resins are copolymers prepared from L-lactide, D-lactide, or a mixture thereof. The lactides are cyclic dimers of lactic acid that can be subjected to a ring-opening polymerization reaction in the presence of a compound having a hydroxyl group such as a hydroxycarboxylic acid. Example hydroxycarboxylic acids are the same as those listed above. In one more specific example, the PLA-based resin is a copolymer of (1) L-lactic acid, D-lactic acid, or a mixture thereof plus (2) glycolic acid.

Other example PLA-based resins can prepared using a combination of (1) a lactic acid (e.g., D-lactic acid, L-lactic acid, or a mixture thereof), (2) an aliphatic polycarboxylic acid (i.e., a compound having at least two carboxylic acid groups), and (3) an aliphatic polyol (i.e., a compound having at least two hydroxyl groups). Yet other PLA-based resins can be prepared using a combination of (1) a lactide (e.g., D-lactide, L-lactide, or a mixture thereof), (2) an aliphatic polycarboxylic acid, and (3) an aliphatic polyol. Suitable polycarboxylic acids and polyols are the same as listed above.

PLA-based resins often contain lactic acid units (i.e., the residue of the lactic acid present in the polymeric material) and other optional units such as hydroxycarboxylic acid units (i.e., the residue of the hydroxycarboxylic acid present in the polymeric material), polycarboxylic acid units (i.e., the residue of the polycarboxylic acid present in the polymeric material), and polyol units (i.e., the residue of the polyol present in the polymeric material). These PLA-based resins often contain at least 50 weight percent lactic acid units. For example, the PLA-based resins can contain at least 60 weight percent, at least 70 weight percent, at least 80 weight percent, at least 90 weight percent, at least 95 weight percent, or at least 98 weight percent lactic acid units.

Suitable PLA-based resins are commercially available under the trade designation INGEO (e.g., INGEO 4032D, INGEO 4043D, and INGEO 4060D) from NatureWorks, LLC (Minnetonka, Minn., USA).

The PLA-based resin can be used as the only polymeric material in the composition or can be combined with another polymeric material such as another polyester resin, a polyolefin (e.g., polyethylene, polypropylene, or copolymers thereof), or the like. In many embodiments, at least 50 weight percent of the polymeric material is a PLA-based resin. For example, the polymeric material can include 50 to 95 weight percent PLA-based resin and 5 to 50 weight percent of another polyester and/or polyolefin, 60 to 95 weight percent PLA-based resin and 5 to 40 weight percent of another polyester and/or polyolefin, or 75 to 95 weight percent PLA-based resin and 5 to 25 weight percent of another polyester and/or polyolefin.

In other embodiments, the polymeric material is a cellulose ester (i.e., a reaction product of cellulose and a carboxylic acid). Example cellulose esters include cellulose acetate, cellulose triacetate, cellulose propionate, cellulose acetate propionate, cellulose tripropionate, cellulose butyrate, cellulose tributryrate, and cellulose acetate butyrate. The various cellulose esters can be prepared with differing solubility depending on the number of hydroxyl groups present. Various cellulose esters are commercially available from Eastman (Kingsport, Tenn., USA).

In yet other embodiments, the polymeric material is a polyvinyl chloride (PVC) resin. The vinyl chloride can be a polymerized to form a homopolymer or copolymer. Suitable co-monomers for formation of copolymers include, for example, ethylenically unsaturated olefins such as those having 2 to 10 carbon atoms or 2 to 6 carbon atoms (e.g., ethylene and propylene), vinyl esters of carboxylic acids such as carboxylic acids having 2 to 10 carbon atoms or 2 to 6 carbon atoms or 2 to 4 carbon atoms (e.g., vinyl acetate, vinyl proprionate, and 2-ethylhexanoic acid vinyl ester), vinyl halides (e.g., vinyl fluoride, vinylidene fluoride, and vinylidene chloride), vinyl ethers (e.g., vinyl methyl ether and vinyl butyl ether), vinyl pyridine, and unsaturated acids (e.g., maleic acid, fumaric acid).

PVC resins often contain at least 50 weight percent vinyl chloride units (i.e., the residue of the vinyl chloride monomer present in the polymeric material). For example, the polyvinyl chloride resin contains at least 60 weight percent, at least 70 weight percent, at least 80 weight percent, at least 90 weight percent, at least 95 weight percent, or at least 98 weight percent vinyl chloride residue.

PVC resins are commercially available under the trade designation OXYVINYLS from OxyChem (Dallas, Tex., USA), under the trade designation FORMOLON from Formosa Plastics (Livingston, N.J., USA), or under the trade designation GEON from PolyOne (Avon Lake, Ohio, USA).

In still another embodiment, the thermoplastic polymeric material is poly(methyl methacrylate) (PMMA) or a copolymer thereof. Copolymers are prepared from a mixture of methyl methacrylate and various optional monomers such as various alkyl (meth)acrylates and (meth)acrylic acid. PMMA is commercially available from under the trade designation ELVACITE from Lucite International (Memphis, Tenn., USA) and under the trade designation PLEXIGLAS from Arkema (Bristol, Pa., USA).

The compositions can be used to provide an adhesive composition. In such compositions, the polymeric material is an elastomeric material. The elastomeric material is often an acrylic polymer such as, for example, one formed using one or more alkyl (meth)acrylate monomers. The acrylic polymer is often a copolymer that if formed from one or more alkyl (meth)acrylate monomers and at least one polar monomer such as, for example, (meth)acrylic acid, hydroxy-substituted alkyl (meth)acrylate monomers, or mixtures thereof.

Any suitable molecular weight can be used for the polymeric material that is combined with the compound of Formula (I). The weight average molecular weight is often at least 1,000 grams/mole, at least 10,000 grams/mole, at least 20,000 grams/mole, at least 50,000 grams/mole, at least 100,000 grams/mole, or at least 200,000 grams/mole. The weight average molecular weight can be up to 1 million grams/mole, up to 800,000 grams/mole, up to 600,000 grams/mole, up to 400,000 grams/mole. For example, the polymeric material can have a weight average molecular weight in a range of 10,000 grams/mole to 1 million grams/mole, in a range of 20,000 grams/mole to 600,000 grams/mole, in a range of 50,000 grams/mole to 500,000 grams/mole, or in a range of 10,000 grams/mole to 100,000 grams/mole.

The compounds of Formula (I) can function as a plasticizer for the polymeric material. A plasticizer is often added to a polymeric material to make the polymeric material more flexible, softer, and more workable (i.e., easier to process). More specifically, the mixture resulting from the addition of the plasticizer to the polymeric material typically has a lower glass transition temperature compared to the polymeric material alone. The glass transition temperature of a polymeric material can be lowered, for example, by at least 30° C., at least 40° C., at least 50° C., at least 60° C., or at least 70° C. by the addition of one or more compounds of Formula (I). The temperature change (i.e., decrease) tends to correlate with the amount of plasticizer added to the polymeric material. It is the lowering of the glass transition temperature that usually leads to the increased flexibility, increased elongation, and increased workability.

The plasticizers of Formula (I) are typically liquids at room temperature (e.g., 20° C. to 25° C.). This is particularly advantageous compared to alkyl 2,5-di-esters of furan dicarboxylates. That is, alkyl 2,5-di-esters of furan dicarboxylates compounds are often solids at room temperature, especially those with alkyl groups having an even number of carbon atoms. Being a liquid at room temperature allows easy mixing of the plasticizer with the polymeric material during processing. For example, the plasticizers can be pumped into an extruder for blending with the polymeric material. The plasticizers of Formula (I) typically do not chemically react with the polymeric material.

Further, the plasticizers of Formula (I) tend to have a low odor due to the low volatility of these compounds. The volatility can be characterized by Thermogravimetric Analysis. When heated at 200° C., the weight loss of the plasticizers of Formula (I) is often less than 10 weight percent or less than 8 weight percent.

In some embodiments, particularly those in which the polymeric compositions will be exposed to an elevated temperature, it may be preferable to include a saturated compound of Formula (IB) rather than the unsaturated compound of Formula (I). The saturated compounds may have a lower tendency to yellow when exposed to elevated temperatures for an extended period of time.

The polymeric compositions that include at least 1 weight percent plasticizer based on the combined weight of the plasticizer and the polymeric material. If the polymeric composition contains less than 1 weight percent or less than 5 weight percent plasticizer, the effect of its addition may not be detected. For example, there may be no change or only a very small change in the glass transition temperature. The polymeric composition can include, for example, at least 5 weight percent, at least 10 weight percent, at least 15 weight percent, at least 20 weight percent, or at least 25 weight percent plasticizer. The amount of plasticizer in the polymeric composition can be up to 75 weight percent based on the combined weight of plasticizer and polymeric material. The upper limit is often determined by the compatibility of the plasticizer with the polymeric material. Some example compositions can include up to 70 weight percent, up to 65 weight percent, up to 60 weight percent, up to 55 weight percent, up to 50 weight percent, up to 45 weight percent, up to 40 weight percent, up to 35 weight percent, up to 30 weight percent, or up to 25 weight percent plasticizer.

Compositions with a thermoplastic polymeric material can contain 1 to 75 weight percent plasticizer and 25 to 99 weight percent polymeric material based on a combined weight of the plasticizer and polymeric material. Some example compositions contain 5 to 75 weight percent plasticizer and 25 to 95 weight percent polymeric material, 5 to 70 weight percent plasticizer and 30 to 95 weight percent polymeric material, 5 to 60 weight percent plasticizer and 40 to 95 weight percent polymeric material, 5 to 50 weight percent plasticizer and 50 to 95 weight percent polymeric material, 5 to 45 weight percent plasticizer and 55 to 95 weight percent polymeric material, 5 to 40 weight percent plasticizer and 60 to 95 weight percent polymeric material, 5 to 30 weight percent plasticizer and 70 to 95 weight percent polymeric material, or 5 to 20 weight percent plasticizer and 80 to 95 weight percent polymeric material.

Compositions with an elastomeric polymeric material for use as an adhesive can contain 70 to 99 weight percent polymeric material and 1 to 30 weight percent plasticizer based on a combined weight of the plasticizer and polymeric material. Some example compositions contain 75 to 99 weight percent polymeric material and 1 to 25 weight percent plasticizer, 80 to 99 weight percent polymeric material and 1 to 20 weight percent plasticizer, or 80 to 95 weight percent polymeric material and 5 to 20 weight percent plasticizer.

Any other optional components can be added to the compositions. Such optional components include, but are not limited to, anti-blocking agents, anti-slip agents, fillers, nucleating agents, thermal stabilizers, light stabilizers, lubricants, pigments, colorants, anti-oxidants, anti-static agents, flame retardants, melt strength enhancers, impact modifiers, and the like. The use of any of these additional optional components may be desirable to provide compositions for specific applications.

Additionally, the plasticizers of Formula (I) can be used in combination with one or more other types of plasticizers such as those that are petroleum-based (i.e., plasticizers that are not based on renewable materials). Some example plasticizers include various phthalate esters such as diethyl phthalate, diisobutyl phthalate, dibutyl phthalate, diisoheptyl phthalate, dioctyl phthalate, diisooctyl phthalate, dinonyl phthalate, diisononyl phthalate, diisodecyl phthalate, and benzylbutyl phthalate; various adipate esters such as di-2-ethylhexyl adipate, dioctyl adipate, diisononyl adipate, and diisodecyl adipate; various phosphate esters such as tri-2-ethylhexyl phosphate, 2-ethylhexyl diphenyl phosphate, trioctylphosphate, and tricresyl phosphate; various trimettitate esters such as tris-2-ethylhexyl trimettitate and trioctyl trimettitate; various sebacate and azelate esters; and various sulfonate esters. Other example plasticizers include polyester plasticizers that can be formed by a condensation reaction of propanediols or butanediols with adipic acid.

Any suitable method of mixing the polymeric material and the plasticizer of Formula (I) can be used such as dry mixing, melt mixing, or mixing in the presence of a suitable solvent (e.g., a solvent that dissolves both the polymeric material and the plasticizer). The mixing can be performed using, for example, a melt extruder, a kneader extruder, a roll mill, a high shear mixer, a twin-screw compounder, or any other processing equipment known in the art. The conditions needed for the mixing are typically well known by those of skill in the art.

In one example mixing method, the polymeric material and the plasticizer of Formula (I) can be mixed in a predetermined weight ratio and then melt extruded. In another example, the polymeric material and the plasticizer are mixed in a predetermined weight ratio and then formed into pellets. The pellets can be used in molding and/or extrusion processing methods to prepare a variety of articles.

Any suitable article can be formed from the mixture. Some example articles are molded objects prepared by processes such as injection molding, compression molding, or the like. Other example articles are fibers formed by spinning methods (e.g., melt spinning) or extrusion. Still other example articles are films prepared by casting from a solvent-containing mixture, by melt compression, by melt extrusion, or the like.

Some of the articles are adhesive articles. Stated differently, the compositions described herein can be adhesive compositions. The adhesive composition can be applied to a surface by melting the adhesive composition into a fluid state. For example, an adhesive layer can be formed on a substrate such as a tape backing by melt extrusion methods.

Extrusion methods tend to cause at least some alignment of the polymeric materials in the composition. This can lead to enhanced modulus from compositions that are extruded rather than solvent cast or compression molded. The modulus can be further enhanced by stretching in the machine direction. Stretching tends to cause further alignment of the polymeric material.

Polymeric films prepared from the compositions can have any desired thickness. The films are often visually clear. The can have a haze less than 5 percent, a transmittance equal to at least 90 percent, and a clarity equal to at least 90 percent using the Test Method 3 (Measurement of Total Transmittance, Haze, and Clarity) described in the Example section. The haze of such film samples is often less than 5 percent, less than 4 percent, less than 3 percent, or less than 2 weight percent. The transmittance and clarity are both often at least 92 percent, at least 94 percent at least 95 percent, at least 96 percent, at least 98 percent, or at least 99 percent. Low haze (e.g., less than 5 percent), high transmittance (e.g., greater than 90 percent), and high clarity (e.g., greater than 90 percent) are typically indicative of good compatibility between the polymeric material and the plasticizer (i.e., the compound of Formula (I)).

Some articles are prepared using a polymeric material that is a plant-based, that is a biodegradable, or both. For example, the polymeric material that is combined with the plasticizer can be a cellulose-based material or a poly(lactic acid)-based material. Such compositions are often desired because both the plasticizer and the polymeric material can be obtained from plant rather than petroleum resources. Stated differently, these compositions can be considered to be environmentally friendly and can be derived from renewable resources.

Some traditional plasticizers (e.g., various phthalic acid esters such as diethyl phthalate) tend to migrate to the outer surface of the article and evaporate due to their relatively high volatility. When these traditional plasticizers evaporate from an article such as a polymeric film containing them, the article can have diminished flexibility compared to its initial flexibility. Additionally, other properties such as tensile strength, tear strength, and elongation to break can be adversely altered. Articles undergoing such changes tend to be characterized as exhibiting poor age stability.

In contrast to both phthalic acid esters with the requisite solubility in hydrophilic polymeric materials (e.g., esters with small alkyl groups such as diethyl phthalate), the compounds of Formula (I) tend to be less volatile and the articles containing them can have improved age stability. Stated differently, the compounds of Formula (I) can provide the same glass transition temperature reduction as many traditional plasticizers but can have improved age stability. The volatility of various plasticizers can be compared by monitoring the weight loss of compositions exposed to elevated temperatures. For example, the compounds of Formula (I) can be heated at 100° C. for up to 96 hours with a weight loss of less than 2 weight percent, less than 1 weight percent, less than 0.8 weight percent, less than 0.6 weight percent, or less than 0.5 weight percent. Polymeric films made using the compounds of Formula (I) as plasticizers can have minimal or no loss of the plasticizer under normal use conditions.

Compared to many commonly used phthalate esters, the compounds of Formula (I) tend to be more compatible with hydrophilic polymeric materials, tend to have a lower volatility, and tend to be more effective in lowering the glass transition temperature. Compared to known alkyl 2,5-di-esters of furan dicarboxylates or alkyl 2,5-di-esters of tetrahydrofuran dicarboxylates, the compounds of Formula (I) tend to be more compatible with hydrophilic polymeric material, have a lower volatility, and are comparably effective in lowering the glass transition temperature.

Various embodiments are provided that are polymeric compositions, articles, or compounds.

Embodiment 1 is a polymeric composition comprising: a) a plasticizer of Formula (I)

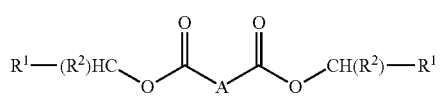

and b) a polymeric material, wherein the plasticizer is compatible with the polymeric material. In Formula (I), A is a divalent group

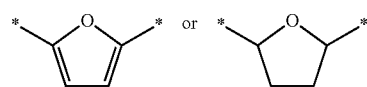 [SMILES: *c1ccc(*)o1 ; *C1CCC(*)O1]

where an asterisk indicates where the group is connected to the rest of the compound. Group $R^1$ is a heteroalkyl having at least one oxy group and group $R^2$ is hydrogen or an alkyl.

Embodiment 2 is the polymeric composition of embodiment 1, wherein $R^1$ is of formula

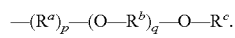

Groups $R^a$ and $R^b$ are each independently an alkylene having 1 to 4 carbon atoms, $R^c$ is an alkyl having 1 to 4 carbon atoms, p is an integer equal to 0 or 1, and q is an integer in a range of 0 to 4.

Embodiment 3 is the polymeric composition of embodiment 1, wherein $R^1$ is tetrahydrofuranyl or tetrahydropryanyl.

Embodiment 4 is the polymeric composition of any one of embodiments 1 to 3, wherein the polymeric material comprises a thermoplastic polymer.

Embodiment 5 is the polymeric composition of any one of embodiments 1 to 4, wherein the polymeric material comprises an aliphatic polyester, a cellulose ester, a polyvinyl chloride, or an acrylic polymer.

Embodiment 6 is the polymeric composition of embodiment 5, wherein the aliphatic polyester is a reaction product of a monomer composition comprising lactic acid.

Embodiment 7 is the polymeric composition of any one of embodiments 1 to 6, wherein the polymeric material is an elastomer.

Embodiment 8 is the polymeric composition of any one of embodiments 1 to 7, wherein the composition comprises 5 to 75 weight percent plasticizer and 25 to 95 weight percent polymeric material.

Embodiment 9 is the polymeric composition of any one of embodiments 1 to 8, wherein the compound of Formula (I) is a liquid at room temperature.

Embodiment 10 is the polymeric composition of any one of embodiments 1 to 9, wherein the compound of Formula (I) is

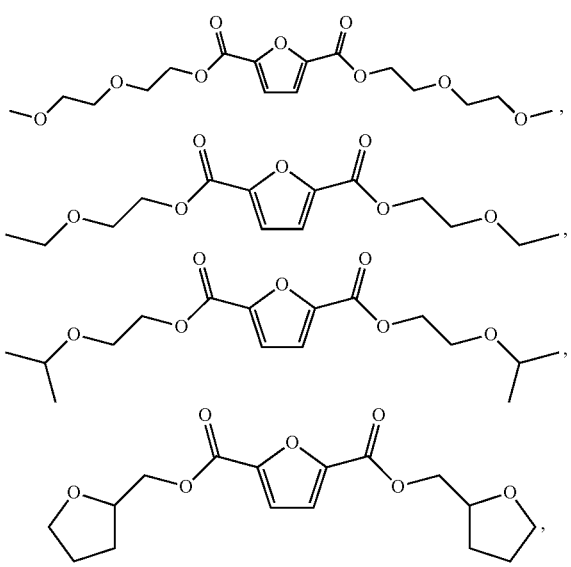

-continued

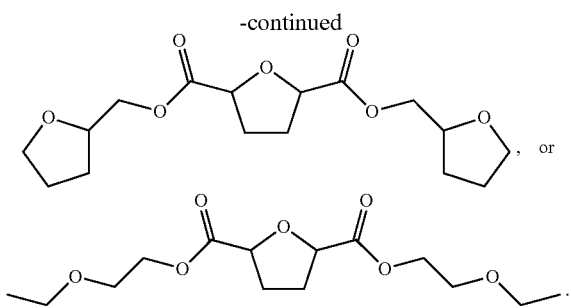
, or

Embodiment 11 is an article comprising the polymeric composition comprising: a) a plasticizer of Formula (I)

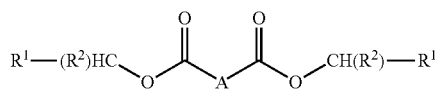 (I)

and b) a polymeric material, wherein the plasticizer is compatible with the polymeric material. In Formula (I), A is a divalent group

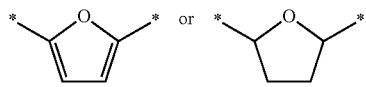

where an asterisk indicates where the group is connected to the rest of the compound. Group $R^1$ is a heteroalkyl having at least one oxy group and group $R^2$ is hydrogen or an alkyl.

Embodiment 12 is the article of embodiment 11, wherein the article is a film or fiber.

Embodiment 13 is the article of embodiment 11 or 12, wherein $R^1$ is of formula

Groups $R^a$ and $R^b$ are each independently an alkylene having 1 to 4 carbon atoms, $R^c$ is an alkyl having 1 to 4 carbon atoms, p is an integer equal to 0 or 1, and q is an integer in a range of 0 to 4.

Embodiment 14 is the article of any one of embodiments 11 to 13, wherein $R^1$ is tetrahydrofuranyl or tetrahydropryanyl.

Embodiment 15 is the article of any one of embodiment 11 to 14, wherein the polymeric material comprises a thermoplastic polymer.

Embodiment 16 is the article of any one of embodiments 11 to 15, wherein the polymeric material comprises an aliphatic polyester, a cellulose ester, a polyvinyl chloride, or an acrylic polymer.

Embodiment 17 is the article of embodiment 16, wherein the aliphatic polyester is a reaction product of a monomer composition comprising lactic acid.

Embodiment 18 is the article of any one of embodiments 11 to 17, wherein the polymeric material is an elastomer.

Embodiment 19 is the article of any one of embodiments 11 to 18, wherein the composition comprises 5 to 75 weight percent plasticizer and 25 to 95 weight percent polymeric material.

Embodiment 20 is the article of any one of embodiments 11 to 19, wherein the compound of Formula (I) is a liquid at room temperature.

Embodiment 21 is the article of any one of embodiments 11 to 20, wherein the compound of Formula (I) is

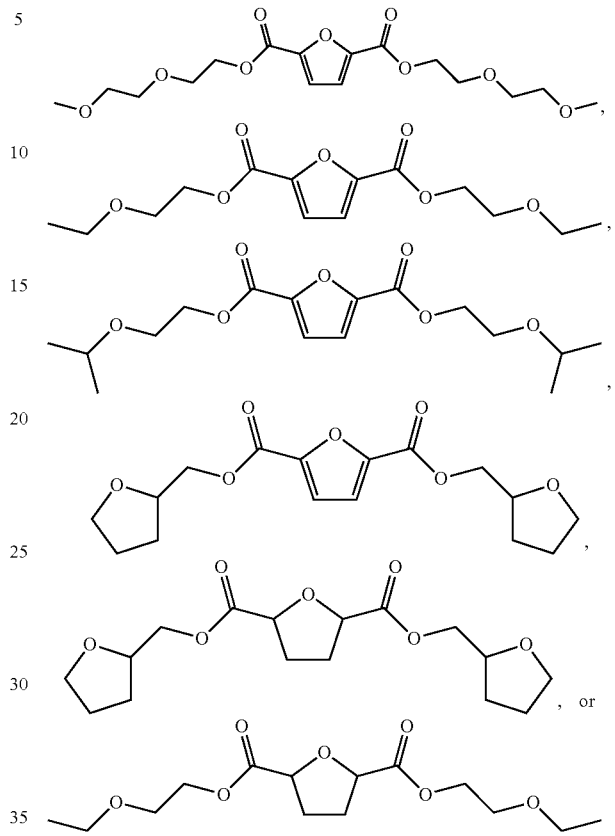

Embodiment 22 is a compound of Formula (I)

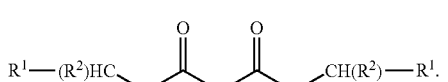 (I)

The group A is a divalent group

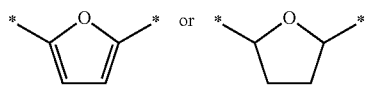 [SMILES: *c1ccc(*)o1 ; *C1CCC(*)O1]

where an asterisk indicates where the group is connected to the rest of the compound. Group $R^1$ is a heteroalkyl having at least one oxy group and group $R^2$ is hydrogen or an alkyl.

Embodiment 23 is the compound of embodiment 22, wherein $R^1$ is of formula

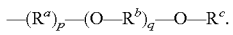

Group $R^a$ and $R^b$ are each independently an alkylene having 1 to 4 carbon atoms, $R^c$ is an alkyl having 1 to 4 carbon atoms, p is an integer equal to 0 or 1, and q is an integer in a range of 0 to 4.

Embodiment 24 is the compound of embodiment 22, wherein $R^1$ is tetrahydrofuranyl or tetrahydropryanyl.

Embodiment 25 is any one of embodiments 22 to 24, wherein the compound of Formula (I) is a liquid at room temperature.

Embodiment 26 is the compound of any one of embodiments 22 to 25, wherein the compound of Formula (I) is

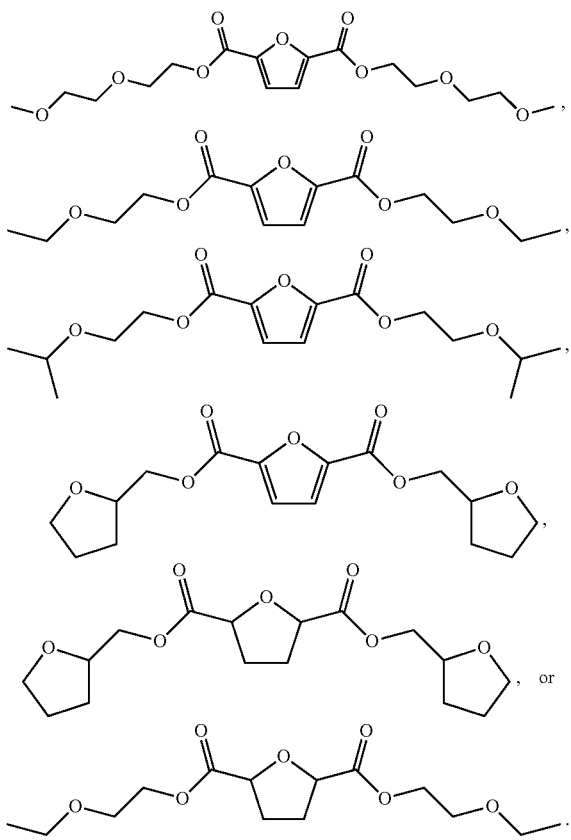

EXAMPLES

As used in the examples, all weights and percentages are by weight unless otherwise specified.

Test Methods

Test Method 1A: Differential Scanning Calorimeter (DSC) Analysis of Films

The specimens were prepared for thermal analysis by weighing and loading the material into TA Instruments aluminum DSC sample pans (Thermal Analysis T080715). The specimens were analyzed using a Modulated Differential Scanning Calorimeter (MDSC) (TA Instruments Q2000 (SN#130, Cell RC-03761), New Castle, Del.) utilizing a heat-cool-heat profile in temperature modulated mode (−40 to 185° C. at 5° C./min with a modulation amplitude of ±0.796° C. and a period of 60 sec). The midpoint (half height) was recorded as the glass transition (Tg) for the second heat profile.

Test Method 1B: Differential Scanning Calorimeter (DSC) Analysis of Films

Approximately 5 to 7 milligrams of a given polymer film was placed in an individual standard aluminum DSC pan (Thermal Analysis T080715), which was then placed in the auto sampler of a dynamic scanning calorimeter (Q2000 DSC, TA Instruments, New Castle, Del.). For each sample analysis, the pan was individually placed on one of the differential posts in the DSC's enclosed cell along with an empty reference pan on the opposite post. Each sample was subjected to a heat-cool-heat profile over a temperature range of −80 to 250° C. at 10° C./min. The midpoint (at half height of the peak) was recorded as the glass transition temperature (Tg) during the second heat profile.

Test Method 2: Percent Haze

The haze was measured using an Ultrascan Pro Spectrophotometer (Hunter Associates Laboratory, Reston, Va.). The instrument was standardized with a diffuse/8° white tile instrument standard (Hunter Associates Laboratory). The film sample was then placed flush with the transmission port on the inside of the instrument. A measurement was taken with a white tile standard followed by a light trap (Hunter Associates Laboratory) on the outside of the unit, and the percent haze was recorded. The measurement was repeated at three different locations on each film sample. The percent haze value result was then calculated as an average of the three measurements.

Test Method 3: Thermo-gravimetric Analysis (TGA) of Plasticizers

The weight loss of the plasticizers was measured by TGA. Approximately 17 to 25 milligrams of a sample was placed in a standard aluminum pan and heated to 500° C. at a rate of 10° C./min using a Model TGA 2950 (TA Instruments, New Castle, Del., USA). The weight loss of each sample was determined at 200° C. and 250° C.

Preparatory Examples 1-6

Preparatory Example 1

A mixture of dimethyl furan 2,5-dicarboxylate (50.61 grams, 0.28 moles, Sarchem Laboratories, Farmingdale, N.J.), diethylene glycol monomethyl ether (142.28 grams, 1.18 moles, Aldrich, Milwaukee, Wis.), and titanium butoxide (1.09 grams, 3.2 mmoles, Aldrich) was placed in a flask with a vigreaux distillation column. The mixture was heated to 190° C. and the distillate liberated from the reaction was collected. After two hours, the mixture was cooled to 50° C. and vacuum was applied (10 mm Hg). After the excess alcohol was removed, the product was filtered through silica gel AND THE PRODUCT WAS COLLECTED AS A yellow oil (23.98 grams).

Preparatory Example 2

A mixture of dimethyl furan 2,5-dicarboxylate (50.35 grams, 0.27 moles), 2-ethoxy ethanol (109.51 grams, 1.21 moles, Alfa Aesar, Ward Hill, Mass.), and titanium butoxide (0.63 grams, 1.85 mmoles) was placed in a flask with a vigreaux distillation column. The mixture was heated to 130° C. and the distillate liberated from the reaction was collected. After two hours, the mixture was cooled to 50° C. and vacuum was applied (10 mm Hg). After the excess alcohol was removed, the vacuum was increased and the product was distilled. A colorless oil was collected at 163-172° C. at 0.15 mm Hg (79.19 grams).

Preparatory Example 3

A mixture of dimethyl furan 2,5-dicarboxylate (41.34 grams, 0.22 moles), isopropoxyethanol (102.56 grams, 0.98 moles, Aldrich), and titanium butoxide (0.41 g, 1.20 mmol) was placed in a flask with a vigreaux distillation column. The mixture was heated to 140° C. and the distillate liberated from the reaction was collected. After three hours, the mixture was cooled to 50° C. and vacuum was applied (10 mmHg). After the excess alcohol was removed, the vacuum was increased and the product was distilled. A yellow oil was collected at 160-161° C. at 0.40 mm Hg (41.70 g).

Preparatory Example 4

A mixture of dimethyl furan 2,5-dicarboxylate (40.06 grams, 0.22 moles), tetrahydrofurfuryl alcohol (90.09 grams, 0.88 moles, Aldrich), and titanium butoxide (0.51 grams, 1.50 mmoles) was placed in a flask with a vigreaux distillation column. The mixture was heated to 170° C. and the distillate liberated from the reaction was collected. After two hours, the mixture was cooled to 50° C. and vacuum was applied (10 mm Hg). After the excess alcohol was removed, the vacuum was increased and the product was distilled. A colorless oil was collected at 178-182° C. at 0.25 mm Hg (57.80 grams). This oil slowly crystallized into a solid. The solid had a melting point of 37-39° C.

Preparatory Example 5

A mixture of dimethyl furan 2,5-dicarboxylate (20.10 grams, 0.11 moles), methanol (250 mL, VWR, West Chester, Pa.), and 5% rhodium on carbon (0.578 grams, Aldrich) was placed in a Parr bottle. The bottle was placed on a Parr hydrogenator and shaken for 17 hours under a hydrogen pressure of 50 pounds per square inch (psi) (345 kPa). The mixture was then filtered through a plug of silica gel and concentrated under vacuum. The crude product was distilled under reduced pressure (82-84° C. at 0.20 mm Hg) to give the product (dimethyl tetrahydrofuran 2,5-dicarboxylate) as a colorless oil (20.10 grams)

A mixture of dimethyl tetrahydrofuran 2,5-dicarboxylate (19.05 grams, 0.10 moles), tetrahydrofurfuryl alcohol (41.25 grams, 0.40 moles), and titanium butoxide (0.24 grams, 0.71 mmoles) was placed in a flask with a vigreaux distillation column. The mixture was heated to 170° C. and the distillate liberated from the reaction was collected. After one hour, the mixture was cooled to 50° C. and vacuum was applied (10 mm Hg). After the excess alcohol was removed, the vacuum was increased and the product was distilled. A colorless oil was collected at 165-185° C. at 0.20 mm Hg (25.07 grams).

Preparatory Example 6

A mixture of dimethyl tetrahydrofuran 2,5-dicarboxylate (20.00 grams, 0.11 moles), 2-ethoxy ethanol (50.34 grams, 0.56 moles), and titanium butoxide (0.20 grams, 0.59 mmoles) was placed in a flask with a vigreaux distillation column. The mixture was heated to 155° C. and the distillate liberated from the reaction was collected. After three hours, the mixture was cooled to 50° C. and vacuum was applied (10 mm Hg). After the excess alcohol was removed, the vacuum was increased and the product was distilled. A colorless oil was collected at 142-145° C. at 0.30 mm Hg (24.90 g).

Thermogravimetric Analysis of Preparatory Examples 1-6

The TGA method (Test Method 3) described above was used to analyze Preparatory Examples 1-6. The weight loss at 200° C. and 250° C. for each sample are shown in Table 1.

TABLE 1

Thermogravimetric Analysis of Plasticizers

| Preparatory Example | Weight loss at 200° C. (wt-%) | Weight loss at 250° C. (wt-%) |
| --- | --- | --- |
| 1 | 1.0 | 6.7 |
| 2 | 4.8 | 36.3 |
| 3 | 6.3 | 40.2 |
| 4 | 2.1 | 18.2 |
| 5 | 3.5 | 23.7 |
| 6 | 7.9 | 57.1 |

Examples 1-6 and Comparative Example C1

Cellulose Acetate (CA) Films

Cellulose acetate (CA 398-30, Eastman Chemical Company, Kingsport Tenn.) was dissolved in acetone at 10.8 weight percent solids. Comparative Example 1 did not include any plasticizer. Examples 1 to 8 were prepared by adding a plasticizer of Preparatory Example 1 to 6 to the cellulose acetate solution. The amount of cellulose acetate solution, the Preparatory Example added, and the amount of the Preparatory Example are shown in Table 2. Each mixture was shaken for 24 hours.

A film was prepared from each solution by knife coating onto a polyester backing using a gap of 0.635 millimeters. After standing at room temperature for 24 hours, the film (approximately 0.04 to 0.07 millimeter thick) was peeled from the backing. The glass transition temperature and haze of the films were determined according to Test Methods 1A and 2.

TABLE 2

Cellulose Acetate Films

| Example | CA solution, grams | Preparatory Example | Preparatory Example, grams | Plasticizer in CA, wt % | Tg, ° C. | Film thickness, mm | Haze, % |
| --- | --- | --- | --- | --- | --- | --- | --- |
| C1 | 15.03 | none | 0 | 193 | 159 | 0.04 | 1.9 |
| 1 | 15.03 | 1 | 0.29 | 15.2 | 126 | 0.06 | 1.6 |
| 2 | 15.00 | 2 | 0.29 | 15.2 | 131 | 0.04 | 1.6 |
| 3 | 15.01 | 3 | 0.30 | 15.6 | 136 | 0.06 | 2.5 |
| 4 | 15.01 | 4 | 0.29 | 15.2 | 132 | 0.06 | 1.9 |
| 5 | 15.01 | 5 | 0.18 | 10.0 | 148 | 0.06 | 1.7 |
| 6 | 15.00 | 5 | 0.29 | 15.2 | 139 | 0.06 | 1.5 |
| 7 | 15.01 | 6 | 0.18 | 10.0 | 128/158 | 0.07 | 1.6 |
| 8 | 15.01 | 6 | 0.29 | 15.2 | 138 | 0.06 | 1.3 |

*Two Tg values observed

Examples 9-18 and C2

Polylactic Acid (PLA) Films

Mixtures of polylactic acid (PLA 4032D, Natureworks, LLC, Minnetonka, Minn.) and plasticizer (Preparatory Examples 1 to 6) were compounded in a Brabender ATR Plasti-Corder (C.W. Brabender Instruments Co., Hackensack, N.J.) at a temperature of 200-210° C. with a mixing speed of 100 rpm. The Preparatory Example and the amount included in each Example 9 to 18 is shown in Table 3. Comparative 2 was prepared in a similar manner but without a plasticizer.

Films were pressed between polyester (PET) films by using 3.5 grams of each polymer resin with 0.254 mm shims in a hot press (Carver 2699, Carver Inc., USA). A clamp force of 6000 pounds (26,700 Newtons) at 200° C. was used to give a final film thickness of 0.24 to 0.27 millimeters. Haze and glass transition temperature of the films were determined according to Test Methods 1B and 2.

TABLE 3

Polylactic Acid Films

| Example | Plasticizer | Plasticizer amount, wt % | Haze, % | Tg, ° C. |
|---|---|---|---|---|
| C2 | none | 0 | 2.9 | 63 |
| 9 | Prep Example 1 | 10 | 3.0 | 43 |
| 10 | Prep Example 1 | 20 | 2.4 | 2 |
| 11 | Prep Example 2 | 10 | 3.7 | 48 |
| 12 | Prep Example 2 | 20 | 1.9 | −1 |
| 13 | Prep Example 3 | 10 | 3.1 | 54 |
| 14 | Prep Example 3 | 20 | 2.1 | 2 |
| 15 | Prep Example 4 | 10 | 2.7 | 49 |
| 16 | Prep Example 4 | 20 | 2.0 | 9 |
| 17 | Prep Example 5 | 10 | 2.3 | 48 |
| 18 | Prep Example 6 | 10 | 4.4 | 43 |

Examples 19-30 and Comparative Example C3

Polyvinyl Chloride (PVC) Films

Mixtures of PVC (poly(vinyl chloride)) resin with a weight average molecular weight of about 62,000 grams/mole (obtained from Aldrich Chemical (Milwaukee, Wis., USA as product number 18958-8), plasticizer of Preparatory Examples 1 to 6, and tetrahydrofuran (VWR) in amounts shown in Table 4 were shaken for 12 hours at room temperature to prepare Examples 19 to 30. Comparative Example C3 was prepared in the same manner but without a plasticizer. The plasticizer used, the amount of plasticizer, the amount of PVC, and the amount of tetrahydrofuran solvent is shown in Table 4. Approximately 5.0 grams of each solution was poured into an aluminum pan and dried at room temperature for 24 hours. All samples were transparent films. The glass transition temperature of each sample was determined according to Test Method 1B and is shown in Table 4.

TABLE 4

PVC Films

| Example | Plasticizer | Plasticizer, grams | PVC, grams | Tetra-hydrofuran, grams | Tg, ° C. |
|---|---|---|---|---|---|
| C3 | none | | | | 83 |
| 19 | Prep example 1 | 1.00 | 4.00 | 20.00 | NA |
| 20 | Prep example 1 | 0.51 | 4.51 | 20.02 | 33 |
| 21 | Prep example 2 | 1.02 | 4.00 | 20.07 | NA |
| 22 | Prep example 2 | 0.53 | 4.50 | 20.02 | 32 |
| 23 | Prep example 3 | 1.00 | 4.00 | 20.03 | NA |
| 24 | Prep example 3 | 0.51 | 4.50 | 20.01 | 27 |
| 25 | Prep example 4 | 1.00 | 4.00 | 20.06 | 24 |
| 26 | Prep example 4 | 0.50 | 4.50 | 20.06 | 34 |
| 27 | Prep example 5 | 0.49 | 4.50 | 21.02 | 34 |
| 28 | Prep example 5 | 1.00 | 4.00 | 20.10 | 28 |
| 29 | Prep example 6 | 0.54 | 4.83 | 20.09 | 67 |
| 30 | Prep example 6 | 1.00 | 4.00 | 20.41 | 60 |

NA: No Tg transition was observed

What is claimed is:

1. A polymeric composition comprising:
   a) a plasticizer selected from

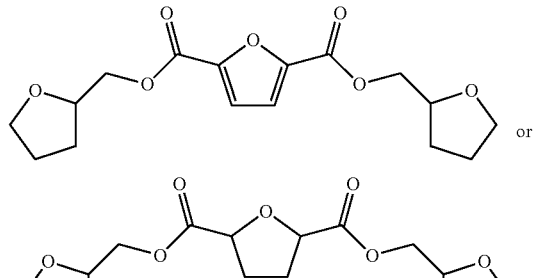

and
   b) a polymeric material; wherein the plasticizer is compatible with the polymeric material.

2. The polymeric composition of claim 1, wherein the polymeric material comprises a thermoplastic polymer.

3. The polymeric composition of claim 1, wherein the polymeric material comprises an aliphatic polyester, a cellulose ester, a polyvinyl chloride, or an acrylic polymer.

4. The polymeric composition of claim 3, wherein the aliphatic polyester is a reaction product of a monomer composition comprising lactic acid.

5. The polymeric composition of claim 1, wherein the polymeric material is an elastomer.

6. The polymeric composition of claim 1, wherein the composition comprises 5 to 75 weight percent plasticizer and 25 to 95 weight percent polymeric material.

7. The polymeric composition of claim 1, wherein the plasticizer is a liquid at room temperature.

8. An article comprising the polymeric composition of claim 1.

9. The article of claim 8, wherein the article is a film or fiber.

10. A compound

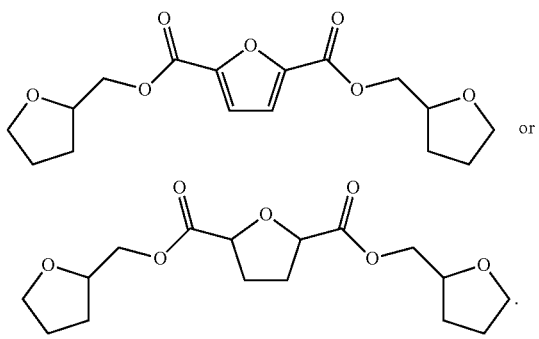

* * * * *

UNITED STATES PATENT AND TRADEMARK OFFICE
CERTIFICATE OF CORRECTION

PATENT NO. : 9,828,489 B2
APPLICATION NO. : 14/914185
DATED : November 28, 2017
INVENTOR(S) : Kevin Lewandowski It is certified that error appears in the above-identified patent and that said Letters Patent is hereby corrected as shown below:

In the Specification

Column 4
Line 50, delete "tranesterification" and insert -- transesterification --, therefor.

Column 5
Line 31, delete "tetrahydrofuryl" and insert -- tetrahydrofurfuryl --, therefor.

Column 7
Line 37, delete "tributryrate," and insert -- tributyrate, --, therefor.
Line 51, delete "proprionate," and insert -- propionate, --, therefor.

Column 10
Line 11, delete "trimettitate" and insert -- trimellitate --, therefor.
Line 12, delete "trimettilate" and insert -- trimellitate --, therefor.
Line 13, delete "trimettilate;" and insert -- trimellitate; --, therefor.

Column 12
Lines 19-20 (approx.), delete "tetrahydropryanyl." and insert -- tetrahydropyranyl. --, therefor.

Column 13
Lines 47-48 (approx.), delete "tetrahydropryanyl." and insert -- tetrahydropyranyl. --, therefor.

Column 14
Line 67, delete "tetrahydropryanyl." and insert -- tetrahydropyranyl. --, therefor.

Column 16
Line 38, delete "vigreaux" and insert -- vigreux --, therefor.
Line 43 (approx.), delete "AND THE PRODUCT WAS COLLECTED AS A" and insert -- and the product was collected as a --, therefor.

Signed and Sealed this
Eighth Day of May, 2018

Andrei Iancu
*Director of the United States Patent and Trademark Office*

CERTIFICATE OF CORRECTION (continued)
U.S. Pat. No. 9,828,489 B2

Line 52, delete "vigreaux" and insert -- vigreux --, therefor.
Line 65, delete "vigreaux" and insert -- vigreux --, therefor.

Column 17
Line 12 (approx.), delete "vigreaux" and insert -- vigreux --, therefor.
Line 36, after "grams)" insert -- . --.
Line 41 (approx.), delete "vigreaux" and insert -- vigreux --, therefor.
Line 54 (approx.), delete "vigreaux" and insert -- vigreux --, therefor.

In the Claims

Column 20
Line 23 (approx.), in Claim 1, delete "material;" and insert -- material, --, therefor.